United States Patent [19]

Dyllick-Brenzinger et al.

[11] Patent Number: 5,738,693
[45] Date of Patent: Apr. 14, 1998

[54] DETECTION OF NAPHTHYLAMINES IN MINERAL OILS

[75] Inventors: Rainer Dyllick-Brenzinger, Weinheim; Ulrike Schlösser, Ludwigshafen; Walter Kurtz, Bad Dürkheim; Gunther Lamm, Hassloch, all of Germany

[73] Assignee: BASF Aktiengesellschaft, Ludwigshafen, Germany

[21] Appl. No.: 602,801

[22] PCT Filed: Aug. 25, 1994

[86] PCT No.: PCT/EP94/02824

§ 371 Date: Mar. 4, 1996

§ 102(e) Date: Mar. 4, 1996

[87] PCT Pub. No.: WO95/07460

PCT Pub. Date: Mar. 16, 1995

[30] Foreign Application Priority Data

Sep. 4, 1993 [DE] Germany .......................... 43 29 953.9

[51] Int. Cl.⁶ .................. G01N 33/28; G01N 31/22; C10L 1/00
[52] U.S. Cl. .................. 44/429; 252/401; 436/56; 436/60; 436/111; 436/112; 508/563; 564/428
[58] Field of Search .................. 44/429; 252/401; 436/56, 60, 111, 112; 508/513; 564/428

[56] References Cited

U.S. PATENT DOCUMENTS

| | | | |
|---|---|---|---|
| 4,209,302 | 6/1980 | Orelup | 44/59 |
| 4,735,631 | 4/1988 | Orelup | 44/59 |
| 4,770,802 | 9/1988 | Ishida et al. | 252/50 |

OTHER PUBLICATIONS

Tomkins et al., Anal. Chem. (1982), 54(1), 91–96.

Primary Examiner—Richard L. Raymond
Attorney, Agent, or Firm—Oblon, Spivak, McClelland, Maier & Neustadt, P.C.

[57] ABSTRACT

A method for detecting naphthylamines which are present as tracers in mineral oils, wherein the naphthylamine is extracted by treating the mineral oil with an aqueous medium, and is coupled in the aqueous phase with a diazonium salt to form an azo dye, the use of specific naphthylamines as tracers in mineral oils and mineral oils containing these specific naphthylamines.

7 Claims, No Drawings

DETECTION OF NAPHTHYLAMINES IN MINERAL OILS

This application is a 371 of PCT/EP94/02824 filed Aug. 25, 1994.

The present invention relates to a novel method for detecting naphthylamines which are present as tracers in mineral oils, wherein the naphthylamine is extracted by treating the mineral oil with an aqueous medium, and is coupled in the aqueous phase with a diazonium salt of an aromatic amine to form an azo dye.

The present invention also relates to the use of specific naphthylamines as tracers for mineral oils and to mineral oils containing these naphthylamines.

U.S. Pat. No. 4,209,302 discloses the use of 1- or 2-(3-morpholinopropylamino)naphthalene, 1- or 2-(3-dimethylaminopropylamino)naphthalene or 1- or 2-(3-diethylaminopropylamino)naphthalene as tracers.

The detection of these compounds is in this case carried out by reacting the appropriate naphthylamines with diazotized 2-chloro-4-nitroaniline. However, it has emerged that this tracer and detection method is not yet completely satisfactory because, inter alia, the stability of the diazonium salt is low.

Anal. Chem., 54 (1982), 91–96, discloses that mineral oils can contain, inter alia, 1- or 2-aminonaphthalenes.

It is an object of the present invention to provide a novel method for detecting mineral oils having naphthylamines as tracers. The novel method ought to be simple to carry out. Moreover, it ought to be possible to render even very small amounts of tracer visible by a strong color reaction. Finally, the tracer should not be removable from the mineral oil by simple extraction with water.

We have found that this object is achieved by detecting the presence of naphthylamines of the formula I

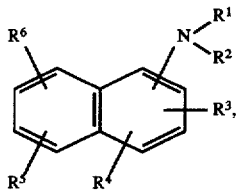

(I)

where $R^1$ and $R^2$ are each, independently of one another, hydrogen, $C_1$–$C_{18}$-alkyl which is unsubstituted or substituted and can be interrupted by 1 to 3 oxygen atoms in ether functionalities or 1 to 3 $C_1$–$C_4$-alkylimino groups, or $C_5$–$C_7$-cycloalkyl, $C_3$–$C_{18}$-alkenyl or unsubstituted or substituted phenyl, or $R^1$ and $R^2$ form, together with the nitrogen atom connecting them, a 5- or 6-membered saturated heterocyclic radical which may have another hetero atom, and $R^3$, $R^4$, $R^5$ and $R^6$ are each, independently of one another, $C_1$–$C_8$-alkyl, benzyl, cyano, nitro, $C_1$–$C_4$-alkanoyl, $C_1$–$C_4$-alkanoylamino, benzoylamino, hydroxysulfonyl or a radical of the formula $OL^1$, $COOL^1$, $NL^1L^2$ or $CONL^1L^2$, where $L^1$ and $L^2$ are each hydrogen, unsubstituted or substituted $C_1$–$C_{18}$-alkyl, $C_5$–$C_7$-cycloalkyl or unsubstituted or substituted phenyl, or $R^3$ together with $R^2$ is $C_3$-alkylene which is unsubstituted or substituted by hydroxyl, and, when the radicals $NR^1R^2$ and $NL^1L^2$ are in the peri positions, $R^1$ and $L^1$ can together also be isopropylidene, in mineral oils in an advantageous way by extracting the naphthylamine of the formula I by treating the mineral oil with an aqueous medium and coupling it in the aqueous phase, in the presence or absence of a buffer, with a diazonium salt derived from an amine from the aminoanthraquinone series to form an azo dye.

All alkyl and alkenyl groups occurring in the naphthylamines may be straight-chain or branched.

For the purposes of the invention, alkenyl radicals essentially have from 1 to 3 double bonds.

Examples of suitable substituents for substituted alkyl groups in the abovementioned formula I are, unless otherwise indicated, hydroxyl, amino, morpholinyl or phenyl. These alkyl groups have, as a rule, 1 or 2 substituents.

Examples of suitable substituents for substituted phenyl groups in the abovementioned formula I are $C_1$–$C_{12}$-alkyl, hydroxyl or $C_1$–$C_4$-alkoxy. These phenyl groups have, as a rule, 1 to 3 substituents.

If $R^1$ and $R^2$ form, together with the connecting nitrogen atom, a 5- or 6-membered saturated heterocyclic radical, which may have another hetero atom, suitable examples thereof are pyrrolidinyl, piperidinyl, morpholinyl, piperazinyl or N-($C_1$–$C_4$-alkyl)-piperazinyl.

Examples of $R^1$, $R^2$, $R^3$, $R^4$, $R^5$, $R^6$, $L^1$, and $L^2$ radicals are methyl, ethyl, propyl, isopropyl, butyl, isobutyl, sec-butyl, tert-butyl, pentyl, isopentyl, neopentyl, tert-pentyl, hexyl, 2-methylpentyl, heptyl, octyl, 2-ethylhexyl or isooctyl.

Further examples of $R^1$, $R^2$, $L^1$ and $L^2$ radicals are 2-hydroxyethyl, 2-hydroxypropyl, 3-hydroxypropyl, 2-hydroxybutyl, 4-hydroxybutyl, 5-hydroxypentyl, 6-hydroxyhexyl, 5-hydroxy-3-oxapentyl, benzyl, 1-phenylethyl, 2-phenylethyl, 2-aminoethyl, 2- or 3-aminopropyl, 2- or 4-aminobutyl, 2-morpholinylethyl, 2- or 3-morpholinylpropyl, 2- or 4-morpholinylbutyl, cyclopentyl, cyclohexyl, cycloheptyl, phenyl, 2-, 3- or 4-methylphenyl, 2-, 3- or 4-ethylphenyl, 2,4-dimethylphenyl, 2-, 3- or 4-methoxyphenyl, 2-, 3- or 4-ethoxyphenyl or 2,4-dimethoxyphenyl.

Further examples of $R^1$ and $R^2$ radicals are nonyl, isononyl, decyl, isodecyl, undecyl, dodecyl, tridecyl, 3,5,5,7-tetramethylnonyl, isotridecyl (the above names isooctyl, isononyl, isodecyl and isotridecyl are trivial names derived from the alcohols obtained from the oxo synthesis—cf. in this connection Ullmanns Encyklopädie der technischen Chemie, 4th Edition, Volume 7, pages 215 to 217, and Volume 11, pages 435 and 436), tetradecyl, pentadecyl, hexadecyl, heptadecyl, octadecyl, 2-methoxyethyl, 2-ethoxyethyl, 2-propoxyethyl, 2-isopropoxyethyl, 2-butoxyethyl, 2- or 3-methoxypropyl, 2- or 3-ethoxypropyl, 2- or 3-propoxypropyl, 2- or 3-butoxypropyl, 2- or 4-methoxybutyl, 2- or 4-ethoxybutyl, 2- or 4-propoxybutyl, 2- or 4-butoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 4,8-dioxadecyl, 3,6,8-trioxadecyl, 3,6,9-trioxaundecyl, 2-dimethylaminoethyl, 2-diethylaminoethyl, 2- or 3-dimethylaminopropyl, 2- or 3-diethylaminopropyl, 2- or 4-dimethylaminopropyl, 2- or 4-diethylaminobutyl, 3,6-dimethyl-3,6-diazaheptyl, 3,6,9-trimethyl-3,6,9-triazadecyl, 2-(1-methoxyethoxy)ethyl, 2-(1-ethoxyethoxy)ethyl, 2-(1-isobutoxyethoxy)ethyl, 2- or 3-(1-methoxyethoxy)propyl, 2- or 3-(1-ethoxyethoxy)propyl, 2- or 3-(1-isobutoxyethoxy)propyl, allyl, prop-1-en-1-yl, methallyl, ethallyl, pentenyl, pentadienyl, hexadienyl, 3,7-dimethylocta-1,6-dien-1-yl, undec-10-en-1-yl, 6,10-dimethylundeca-5,9-dien-2-yl, 3,7,11-trimethyldodeca-1,6,10-trien-1-yl, 3,7,11-trimethyldodeca-2,6,10-trien-1-yl, octadec-9-en-1-yl, octadeca-9,12-dien-1-yl, octadeca-9,12,15-trien-1-yl or 6,10,14-trimethylpentadeca-5,9,13-trien-2-yl.

Further examples of $R^3$, $R^4$, $R^5$ and $R^6$ radicals are formyl, acetyl, propionyl, butyryl, isobutyryl, formylamino, acetylamino, propionylamino, butyrylamino, isobutyrylamino, hydroxyl, methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, heptyloxy, octyloxy, isooctyloxy, 2-ethylhexyloxy, amino, mono- or dimethylamino, mono- or diethylamino, mono- or dipropylamino, mono- or diisopropylamino, mono- or dibutylamino, N-methyl-N-ethylamino, mono- or dicyclohexylamino, N-methyl-N-cyclohexylamino, phenylamino, N-phenyl-N-methylamino, carbamoyl, mono- or dimethylcarbamoyl, mono- or diethylcarbamoyl, mono- or dipropylcarbamoyl, mono- or diisopropylcarbamoyl, mono- or dibutylcarbamoyl, N-methyl-N-ethylcarbamoyl, phenylcarbamoyl, methoxycarbonyl, ethoxycarbonyl, propoxycarbonyl, isopropoxycarbonyl, butoxycarbonyl or phenoxycarbonyl.

Examples of $R^2$ and $R^3$ radicals together are 1,3-propylene or 2-hydroxy-1,3-propylene.

A preferred method is for the detection of naphthylamines of the formula I where
  $R^1$ and $R^2$ are each, independently of one another, hydrogen, $C_1$–$C_{15}$-alkyl which is unsubstituted or substituted and can be interrupted by 1 to 3 oxygen atoms in ether functionalities, cyclohexyl, unsubstituted or substituted phenyl, or $R^1$ and $R^2$ form, together with the nitrogen atom connecting them, a 5- or 6-membered saturated heterocyclic radical which may have another hetero atom, and
  two of the $R^3$, $R^4$, $R^5$ and $R^6$ radicals are each hydrogen and the other two are each, independently of one another, hydrogen, $C_1$–$C_4$-alkyl, $C_1$–$C_4$-alkoxy, hydroxyl, nitro, $C_1$–$C_4$-alkanoylamino, benzoylamino, a radical of the formula $NL^1L^2$ where $L^1$ and $L^2$, independently of one another, are each hydrogen or $C_1$–$C_4$-alkyl, or cyano or carboxyl, and, when the radicals $NR^1R^2$ and $NL^1L^2$ are in the peri positions, $R^1$ and $L^1$ can together also be isopropylidene.

A particularly preferred method is for the detection of naphthylamines of the formula I where $R^1$ is hydrogen, $R^2$ is $C_1$–$C_{15}$-alkyl which can be interrupted by 1 to 3 oxygen atoms in ether functionalities, or cyclohexyl, and one of the $R^3$, $R^4$, $R^5$ and $R^6$ radicals is hydroxyl or $C_1$–$C_4$-alkoxy and the others are hydrogen.

A preferred method for detecting naphthylamines of the formula I is also one in which a naphthylamine of the formula I is extracted by treating the mineral oil with a, preferably acidic, aqueous solution of a diazonium salt derived from an amine from the aminoanthraquinone series, and subsequently, in the presence or absence of a buffer, coupled with the diazonium salt to form an azo dye.

1-Aminoanthraquinone is particularly emphasized as amine from the anthraquinone series.

Mineral oils mean for the purposes of the invention for example fuels such as gasoline, kerosine or diesel oil, or oils such as heating oil or engine oil.

As tracers in mineral oil, the naphthylamines of the formula I are used either as such or in the form of solutions. Suitable and preferred solvents are aromatic hydrocarbons such as dodecylbenzene, diisopropylnaphthalene or a mixture of higher aromatic compounds commercially available under the name Shellsol® AB (from Shell). To avoid the resulting solutions having a high viscosity, the concentration of naphthylamine I is generally chosen to be from 30 to 50% of the weight of the solution.

It is very simple by means of the method according to the invention to detect the naphthylamines of the formula I in mineral oils even if the tracers are present in a concentration of only about 10 ppm or below.

Examples of suitable acids for an acidic aqueous solution of a diazonium salt for extraction of the naphthylamine of the formula I are inorganic or organic acids, such as hydrochloric acid, sulfuric acid, nitric acid, phosphoric acid, formic acid, acetic acid or propionic acid. The acidic aqueous solutions generally have an acid concentration of from 0.5 to 20% by weight.

Examples of suitable aqueous media for extraction of the naphthylamines of the formula I from the mineral oil are water or mixtures of water with acids and/or water-miscible organic solvents and/or inorganic substances.

Suitable acids for this purpose are the abovementioned acids in the stated concentration.

Examples of water-miscible organic solvents are alcohols such as methanol, ethanol, propanol, isopropanol, ethylene glycol or 1,2-propylene glycol, ethers such as 2-methoxyethanol, 2-ethoxyethanol, 2-butoxyethanol, 2-(2-methoxyethoxy)ethanol, 1-methoxy-2-propanol or tetrahydrofuran, carboxamides such as N,N-dimethylformamide or N-methylpyrrolidone, propylene carbonate, dimethyl sulfoxide or sulfolane. The content of water-miscible organic solvent is in general from 1 to 50% of the weight of the aqueous medium.

Examples of inorganic substances are salts such as alkali metal halides, aluminum halides, zinc halides or ammonium salts.

It is preferred to use aqueous acid, which may also contain a water-miscible organic solvent, as aqueous medium.

In order to obtain an optimal coupling reaction taking place in the presence or absence of a solvent, and a resulting optimization of the yield of azo dye, it is advisable to control the pH by using buffer substances and to use the reactants in a favorable molar ratio (naphthylamine:diazonium salt 1:500 to 1:10, preferably 1:100 to 1:20).

Examples of suitable buffer substances are alkali metal acetates, monoalkali metal citrates and alkali metal dihydrogen phosphates, particular mention being made in each case of the sodium salts, or those buffer systems mentioned in the Handbook of Chemistry and Physics, 65th Ed., 1984–1985, pages D148 to D150.

Anions suitable as counter ions to the diazonium cations are the anions conventional for this purpose, such as chloride, hydrogen sulfate, sulfate, dihydrogen phosphate, monohydrogen phosphate, phosphate, tetrafluoroborate, tetrachlorozincate or acetate.

It is advantageous in some cases also to add small amounts of alkali metal salts of arylsulfonic acids, eg. the sodium salt of naphthalene-1,5-disulfonic acid, as stabilizer for the diazonium salts.

Used a rule for the detection reaction is an aqueous solution of a diazonium salt which contains from 0.1 to 2% by weight, based on the solution, of diazonium salt. Moreover, in general from 0.01 to 1 part by weight of diazonium salt solution is used per 1 part by weight of mineral oil with tracer.

It is furthermore advantageous for detecting naphthylamines of the formula I in mineral oils if the naphthylamine of the formula I is extracted by treating the mineral oil with an aqueous medium, and is coupled in the aqueous phase, in the presence or absence of a buffer, with a diazonium salt derived from an amine from the aminoanthraquinone series and is in the solid state of aggregation on a carrier to form an azo dye.

Suitable carriers are inorganic materials such as active carbon, molecular sieves, kiesel guhr, titanium dioxide, aluminum oxide or calcium chloride, or organic materials such as cellulose fibers, cotton, wood pulp, polystyrene or polyvinyl chloride.

After addition of the diazonium salt on the carrier to the aqueous extract of the naphthylamine of the formula I, the diazonium salt dissolves completely or partially and is thus made available for the azo coupling.

Another suitable carrier is a strip of paper, eg. of filter paper. It can be impregnated with a solution of one of the abovementioned diazonium salts and dried. (In this case it is possible to prevent decomposition of the diazonium salt by storing the impregnated strips of paper in the dry and dark).

On immersion of such an impregnated strip of paper into the aqueous extract, a color reaction takes place on its surface owing to the formation of an azo dye. It is possible in this way to detect the naphthylamines of the formula I in an extremely simple manner.

An advantageous method also comprises adding a few shreds of the impregnated strip of paper to the aqueous extract and briefly heating if necessary.

It has proven advantageous to detect the naphthylamines of the formula I using a "diazo paper" or a "diazo sheet". These diazo indicators are prepared by impregnating paper, eg. filter paper, or a thin-layer chromatography sheet which is coated, for example, with cellulose, with the appropriate diazonium salt solution, leaving untreated the region which on development comes into direct contact with the aqueous extract. Immersion of a strip of paper or sheet prepared in this way in the aqueous extract allows the yield of azo dye to be optimized in the manner of a paper chromatography. The azo dye which is formed remains at the start, and its concentration is increased by the continuous supply of new naphthylamine, and it is thus easy to detect.

The naphthylamines of the formula I are conventional products from the manufacture of dyes. They are easily obtainable.

The present invention furthermore relates to the use of naphthylamines of the formula Ia

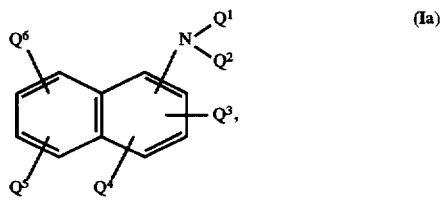

(Ia)

where $Q^1$ and $Q^2$ are each, independently of one another, hydrogen, $C_1$–$C_{18}$-alkyl, which can be interrupted by 1 to 3 oxygen atoms in ether functionalities, $C_5$–$C_7$-cycloalkyl, $C_3$–$C_{18}$-alkenyl, unsubstituted or substituted phenyl, or $Q^1$ and $Q^2$ form, together with the nitrogen atom connecting them, a 5- or 6-membered saturated heterocyclic radical which may have oxygen as further hetero atom, and $Q^3$, $Q^4$, $Q^5$ and $Q^6$ are each, independently of one another, hydrogen, $C_1$–$C_8$-alkyl, benzyl, cyano, nitro, $C_1$–$C_4$-alkanoyl, $C_1$–$C_4$-alkanoylamino, benzoylamino, hydroxysulfonyl or a radical of the formula $OZ^1$, $COOZ^1$, $NZ^1Z^2$ or $CONZ^1Z^2$, where $Z^1$ and $Z^2$ are each hydrogen, $C_1$–$C_8$-alkyl, which may be substituted by hydroxyl or phenyl, or $C_5$–$C_7$-cycloalkyl or unsubstituted or substituted phenyl, or $Q^3$ together with $Q^2$ is $C_3$-alkylene, which is unsubstituted or substituted by hydroxyl, and, when the radicals $NR^1R^2$ and $NZ^1Z^2$ are in the peri positions, $R^1$ and $Z^1$ can together also be isopropylidene, for use as tracers in mineral oils.

For lists of examples of the $Q^1$ to $Q^6$ radicals, reference may be made to the preceding statements relating to the $R^1$ to $R^6$ radicals.

Naphthylamines of the formula Ia which are preferably used as tracers in mineral oils are those in which $Q^1$ and $Q^2$ are each, independently of one another, hydrogen, $C_1$–$C_{15}$-alkyl which may be interrupted by 1 to 3 oxygen atoms in ether functionalities, cyclohexyl or unsubstituted or substituted phenyl, and two of the $Q^3$, $Q^4$, $Q^5$ and $Q^6$ radicals are each hydrogen and the other two are each, independently of one another, hydrogen, $C_1$–$C_4$-alkyl, $C_1$–$C_4$-alkoxy, hydroxyl, nitro, cyano or carboxyl.

Naphthylamines of the formula Ia which are particularly preferably used as tracers in mineral oils are those in which $Q^1$ is hydrogen, $Q^2$ is $C_1$–$C_{15}$-alkyl which can be interrupted by 1 to 3 oxygen atoms in ether functionalities, or cyclohexyl, and one of the $Q^3$, $Q^4$, $Q^5$ and $Q^6$ radicals is hydroxyl or $C_1$–$C_4$-alkoxy and the others are hydrogen.

For the purposes of the invention, the use of naphthylamines of the formula Ia as tracers means addition thereof in concentrations such that this causes absolutely no change visible to the human eye in the mineral oils, but the naphthylamines of the formula Ia can be detected easily and clearly visibly by the detection methods described in detail herein.

The naphthylamines of the formula Ia are particularly suitable as tracers in mineral oils for which identification is required, eg. for tax reasons. In order to keep the costs of identification low, it is moreover desirable to use the minimum quantities of tracer.

The use of the naphthylamines of the formula Ia as tracers in mineral oils can take place, for example, by the method as has been described above in detail for the naphthylamines of the formula I.

The naphthylamines of the formula Ia used as tracers in mineral oils are advantageously detected by extracting the naphthylamine of the formula Ia by treating the mineral oil with an aqueous medium, and coupling it in the aqueous phase, in the presence or absence of a buffer, with a diazonium salt, which is derived from an amine from the aminoanthraquinone, aminonaphthalene, aniline, aminothiophene, aminothiazole or aminobenzoisothiazole series, to form an azo dye.

The naphthylamines of the formula Ia used as tracers in mineral oils are particularly advantageously detected by extracting the naphthylamine of the formula Ia by treating the mineral oil with a, preferably, acidic, aqueous solution of a diazonium salt derived from an amine from the aminoanthraquinone, aminonaphthalene, aniline, aminothiophene, aminothiazole or aminobenzoisothiazole series, and subsequently coupling it, in the presence or absence of a buffer, with the diazonium salt to form an azo dye.

As explained above in detail, it is also possible to employ a procedure in which the diazonium salts are in the solid state of aggregation on a carrier.

1-Aminoanthraquinone is particularly emphasized as amine from the anthraquinone series.

Suitable aminonaphthalenes have, for example, the formula II

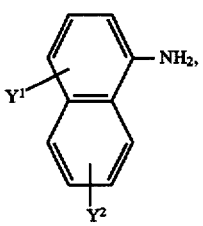
(II)

where $y^1$ and $y^2$ are each, independently of one another, hydrogen, hydroxyl or hydroxysulfonyl.

Suitable anilines have, for example, the formula III

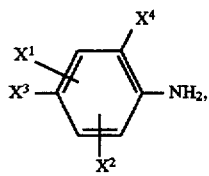
(III)

where $X^1$ is hydrogen, halogen, $C_1$–$C_4$-alkoxy, nitro or hydroxysulfonyl, $X^2$ is hydrogen, halogen, $C_1$–$C_4$-alkoxy, cyano, nitro, or phenylazo which is unsubstituted or substituted by methyl, ethyl, methoxy or ethoxy and $X^3$ is hydrogen, $C_1$–$C_4$-dialkylamino, pyrrolidinyl, piperidinyl, morpholinyl, nitro or hydroxysulfonyl and $X^4$ is hydrogen, halogen, cyano or a heterocyclic radical, eg. 3-phenyl-1,2,4-oxadiazol-5-yl.

Suitable aminothiophenes, aminothiazoles or aminobenzoisothiazoles have, for example, the formula

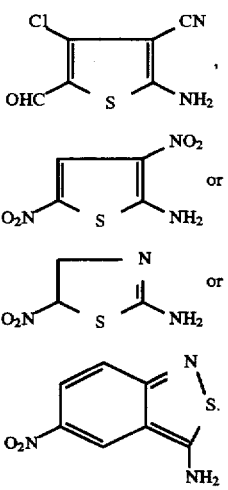
(IV)

(V)

(VI)

(VII)

Concerning the individual parameters for the detection reactions, reference may be made to the statements made above about the naphthylamines of the formula I.

The naphthylamines of the formula Ia can, of course, also be detected in the mineral oils by conventional physical analytical methods, for example by gas chromatography, by pressure liquid chromatography, thin-layer chromatography or column chromatography.

The present invention further relates to mineral oils containing one or more naphthylamines of the formula Ia, excluding 1-aminonaphthalene and 2-aminonaphthalene.

The following examples illustrate the invention.

a) Preparation of the Reagent Solutions

Reagent solution B

Aqueous diazotization of 2-(3-phenyl-1,2,4-oxadiazol-5-yl)aniline with sodium nitrite resulted in a 0.11 molar aqueous diazonium chloride solution with a pH of about 1.1.

b) General Detection Reaction in Acidic Solution

The particular naphthylamine was dissolved at a concentration of 50 ppm in diesel fuel and further diluted with Shellsol® AB (from Shell) to a concentration of 5 ppm. 0.9 part by volume of this solution was vigorously shaken with 0.1 part by volume of reagent solution for 1 min. The lower aqueous phase was then inspected. Alternatively, it is also possible to add from 0.1 to 0.3 part by volume of 50% by weight acetic acid to the aqueous phase. This ensures that the resulting dye is completely dissolved and the full strength of its color is revealed.

c) General Detection Reaction in Buffered Aqueous Solution 10 g of the diesel fuel containing 10 ppm tracer are extracted with 1 g of 9% by weight hydrochloric acid, the aqueous phase is neutralized with sodium hydroxide solution, and four times the amount of one of the three following buffer solutions 1, 2 and 3 is added.

Buffer solution 1: 5% by weight aqueous citric acid solution adjusted to pH 3.3 with 10% by weight sodium hydroxide solution.

Buffer solution 2: 5% by weight aqueous potassium dihydrogen phosphate solution of pH 4.4.

Buffer solution 3: 5% by weight aqueous sodium acetate trihydrate solution of pH 8.2.

Subsequently, 0.1 g of reagent solution A is added.

The azo couplings usually take place quite rapidly but they can in most cases be speeded up by briefly heating.

The results of the investigations are listed in the following tables. Either the intensity of the color is assessed by a score (from 1 to 5; 1: no color, 5: very intense color) or the extinction is reported. It is also indicated whether the color reaction takes place immediately. Finally, the shade of the color of the resulting azo compound or, in some cases, its absorption maximum is also stated.

TABLE 1

Detection in buffered solution

| Example No. | Naphthylamine | REAGENT SOLUTION A | | |
|---|---|---|---|---|
| | | Buffer 1 | Buffer 2 | Buffer 3 |
| 1 | 1-naphthyl-NH—C$_3$H$_6$—OCH$_3$ | 5<br>violet<br>immediate | 5<br>violet<br>immediate | 2<br>orange<br>immediate |
| 2 | 1-naphthyl-NH—C$_3$H$_6$—O—C$_2$H$_4$—OCH$_3$ | 5<br>violet<br>immediate | 5<br>violet<br>immediate | 2<br>orange<br>immediate |
| 3 | 1-naphthyl-NH—C$_2$H$_4$—O—C$_2$H$_4$—O—C$_2$H$_4$—OCH$_3$ | 5<br>violet<br>immediate | 4<br>bluish red<br>immediate | 2<br>orange<br>immediate |
| 4 | 1-naphthyl-NH—C$_3$H$_6$—O—C$_2$H$_4$—OC$_4$H$_9$ | 5<br>violet<br>immediate | 5<br>orange<br>immediate | 3<br>yellow<br>immediate |
| 5 | 2-naphthyl-NH-i-C$_{13}$—H$_{27}$ | 3<br>violet<br>immediate | 2<br>orange<br>immediate | 2<br>orange<br>immediate |
| 6 | 2-naphthyl-NH—CH$_2$—CH(C$_2$H$_5$)(C$_4$H$_9$) | 1 | 1 | 1 |
| 7 | 1-naphthyl-NH—C$_2$H$_5$ | 520 nm<br>1.30<br>red<br>immediate | 470 nm<br>0.77<br>orange<br>immediate | 437 nm<br>0.35<br>orange<br>immediate |

TABLE 1-continued

Detection in buffered solution

| Example No. | Naphthylamine | REAGENT SOLUTION A | | |
|---|---|---|---|---|
| | | Buffer 1 | Buffer 2 | Buffer 3 |
| 8 | [structure: naphthalene with NH$_2$ and OC$_2$H$_5$] | 5<br>red<br>immediate | 4<br>red<br>immediate | 3<br>orange<br>immediate |
| 9 | [structure: naphthalene with NH—C$_2$H$_5$] | 582 nm<br>0.43<br>violet<br>immediate | 580 nm<br>0.65<br>violet<br>immediate | 575 nm<br>0.59<br>violet<br>immediate |
| 10 | [structure: naphthalene with NH$_2$] | 473 nm<br>0.60 | 4<br>orange<br>immediate | 4<br>orange<br>immediate |
| 11 | [structure: naphthalene with OH, NH side chain, and HO] | 1 | 1 | 1 |
| 12 | [structure: naphthalene with NH$_2$ and HO] | 493 nm<br>0.68<br>3<br>orange<br>immediate | 473 nm<br>0.699<br>3<br>orange<br>immediate | 469 nm<br>0.57<br>3<br>orange<br>immediate |
| 13 | [structure: naphthalene with NH$_2$ and OH] | 516 nm<br>0.41<br>4<br>red<br>immediate | 525 nm<br>0.46<br>4<br>red<br>immediate | 545 nm<br>0.47<br>3<br>orange<br>immediate |

TABLE 1-continued

Detection in buffered solution

| Example No. | Naphthylamine | REAGENT SOLUTION A | | |
|---|---|---|---|---|
| | | Buffer 1 | Buffer 2 | Buffer 3 |
| 14 | 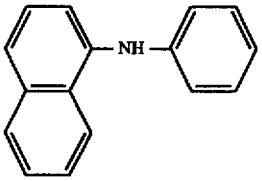 | 3 orange immediate | 3 orange immediate | 3 orange immediate |
| 15 | 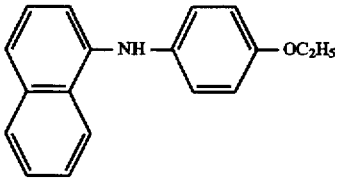 | 1 | 1 | 1 |
| 16 | 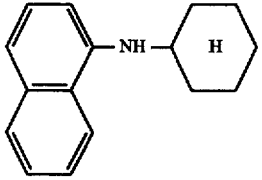 | 4 lilac immediate | 4 lilac immediate | 1 |
| 17 | 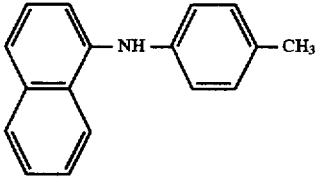 | 3 orange immediate | 3 orange immediate | 3 orange immediate |
| 18 | 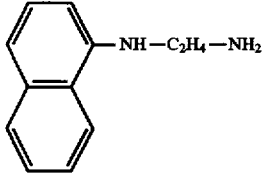 | 5 violet immediate | 4 pink immediate | 3 yellow immediate |

TABLE 2

Detection reaction in acidic solution

| Example No. | Naphthylamine | REAGENT SOLUTION A | REAGENT SOLUTION B |
|---|---|---|---|
| 19 | 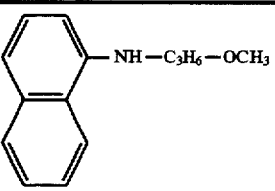 | 4 violet immediate | no reaction |

TABLE 2-continued

Detection reaction in acidic solution

| Example No. | Naphthylamine | REAGENT SOLUTION A | REAGENT SOLUTION B |
|---|---|---|---|
| 20 | 1-naphthyl—NH—C$_3$H$_6$—O—C$_2$H$_4$—OCH$_3$ | 5 violet immediate | no reaction |
| 21 | 1-naphthyl—NH—(C$_2$H$_4$—O)$_3$—CH$_3$ | 5 violet immediate | no reaction |
| 22 | 1-naphthyl—NH—C$_3$H$_6$—O—C$_2$H$_4$—O—C$_4$H$_9$ | 4 violet immediate | no reaction |
| 23 | 2-naphthyl—NH-i-C$_{13}$—H$_{27}$ | 2 pink immediate | no reaction |
| 24 | 2-naphthyl—NH—CH$_2$—CH(C$_2$H$_5$)(C$_4$H$_9$) | 2 pink immediate | no reaction |
| 25 | 1-naphthyl—NH—C$_2$H$_5$ | 4 red immediate | 2 orange slow |
| 26 | naphthyl (NH$_2$, OC$_2$H$_5$) | 5 violet immediate | no reaction |

TABLE 2-continued

Detection reaction in acidic solution

| Example No. | Naphthylamine | REAGENT SOLUTION A | REAGENT SOLUTION B |
|---|---|---|---|
| 27 | 2-(ethylamino)naphthalene (NH—C$_2$H$_5$) | 5 violet immediate | 5 violet fast |
| 28 | 1-naphthylamine (NH$_2$) | 5 red-violet immediate | 5 violet fast |
| 29 | 1-(2-hydroxy-3-aminopropyl)-6-hydroxynaphthalene (OH, NH, HO) | 5 violet immediate | no reaction |
| 30 | 2-amino-6-hydroxynaphthalene (NH$_2$, HO) | 5 red immediate | no reaction |
| 31 | N-phenyl-1-naphthylamine | 2 pink immediate | no reaction |
| 32 | N-(4-ethoxyphenyl)-1-naphthylamine (OC$_2$H$_5$) | 2 pink immediate | no reaction |
| 33 | N-(4-methylphenyl)-1-naphthylamine (CH$_3$) | 2 pink immediate | no reaction |

TABLE 2-continued

Detection reaction in acidic solution

| Example No. | Naphthylamine | REAGENT SOLUTION A | REAGENT SOLUTION B |
|---|---|---|---|
| 34 | 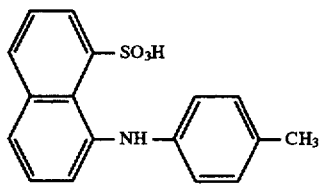 NH—CH$_2$—CH$_2$—NH$_2$ | 5<br>violet<br>immediate | 5<br>violet<br>fast |

EXAMPLE 35

1.5 ml of a diesel oil with 10 ppm tolylperi acid of the formula

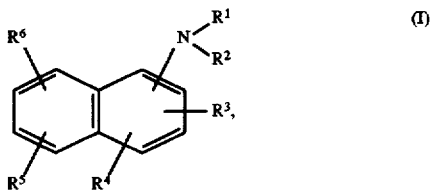

as tracer were mixed in a reaction vessel with 3 drops of a solution of 100 ppm disodium hydrogen phosphate in deionized water. This mixture was vigorously shaken for 20 sec and then the phases were allowed to separate. The upper oily phase was yellow and cloudy, and the lower had a trace of yellow. To this two-phase mixture were cautiously added 2 drops of a 1% by weight aqueous solution of the diazonium bisulfate from 1-aminoanthraquinone.

It is important to add the diazonium salt solution in such a way that three phases form. The reaction vessel should also not be shaken after addition of the diazonium salt solution. A clearly visible black ring then forms at the interface between the diazonium salt and phosphate buffer solutions. Repetion of the same test with a heating oil without tracer results in a colorless aqueous phase and no black ring.

We claim:

1. A method for detecting the presence of naphthylamines of the formula I $$\text{(I)}$$

(structure showing naphthalene with substituents R$^1$, R$^2$, R$^3$, R$^4$, R$^5$, R$^6$ and N)

where $R^1$ and $R^2$ are each, independently of one another, hydrogen, $C_1$–$C_{18}$-alkyl which is unsubstituted or substituted and can be interrupted by 1 to 3 oxygen atoms in ether functionalities or 1 to 3 $C_1$–$C_4$-alkylimino groups, or $C_5$–$C_7$-cycloalkyl, $C_3$–$C_{18}$-alkenyl or unsubstituted or substituted phenyl, or $R^1$ and $R^2$ form, together with the nitrogen atom connecting them, a 5- or 6-membered saturated heterocyclic radical which may have another hetero atom, and $R^3$, $R^4$, $R^5$ and $R^6$, are each, independently of one another, hydrogen, $C_1$–$C_8$-alkyl, benzyl, cyano, nitro, $C_1$–$C_4$-alkanoyl, $C_1$–$C_4$-alkanoylamino, benzoylamino, hydroxysulfonyl or a radical of the formula OL$^1$, COOL$^1$, NL$^1$L$^2$ or CONL$^1$L$^2$, where L$^1$ and L$^2$ are each hydrogen, unsubstituted or substituted $C_1$–$C_{18}$-alkyl, $C_5$–$C_7$-cycloalkyl or unsubstituted or substituted phenyl, or $R^3$ together with $R^2$ is $C_3$-alkylene which is unsubstituted or substituted by hydroxyl, and, when the radicals NR$^1$R$^2$ and NL$^1$L$^2$ are in the peri positions, R$^1$ and L$^1$ can together also be isopropylidene in mineral oils, which comprises extracting the naphthylamine of the formula I by treating the mineral oil with an aqueous medium and coupling it in the aqueous phase, in the presence or absence of a buffer, with a diazonium salt derived from an amine from the aminoanthraquinone series to form an azo dye and detecting the presence of said azo dye on the basis of color change observed.

2. A method as claimed in claim 1, wherein $R^1$ and $R^2$ are each, independently of one another, hydrogen, $C_1$–$C_{15}$-alkyl which is unsubstituted or substituted and can be interrupted by 1 to 3 oxygen atoms in ether functionalities, cyclohexyl, unsubstituted or substituted phenyl, or $R^1$ and $R^2$ form, together with the nitrogen atom connecting them, a 5- or 6-membered saturated heterocyclic radical which may have another hetero atom, and two of the $R^3$, $R^4$, $R^5$ and $R^6$ radicals are each hydrogen and the other two are each, independently of one another, hydrogen, $C_1$–$C_4$-alkyl, $C_1$–$C_4$-alkoxy, hydroxyl, nitro, $C_1$–$C_4$-alkanoylamino, benzoylamino, a radical of the formula NL$^1$L$^2$ where L$^1$ and L$^2$, independently of one another, are hydrogen or $C_1$–$C_4$-alkyl, or cyano or carboxyl, and, when the radicals NR$^1$R$^2$ and NL$^1$L$^2$ are in the peri positions, R$^1$ and L$^1$ can together also be isopropylidene.

3. A method as claimed in claim 1, wherein R$^1$ is hydrogen, R$^2$ is $C_1$–$C_{15}$-alkyl which can be interrupted by 1 to 3 oxygen atoms in ether functionalities, or cyclohexyl and one of the R$^3$, R$^4$, R$^5$ and R$^6$ radicals is hydroxyl or $C_1$–$C_4$-alkoxy and the others are hydrogen.

4. A method as claimed in claim 1, wherein the naphthylamine of the formula I is extracted by treating the mineral oil with an aqueous solution of a diazonium salt derived from an amine from the aminoanthraquinone series, and subsequently, in the presence or absence of a buffer, coupled with the diazonium salt to form an azo dye.

5. A mineral oil composition comprising mineral oil and an effective tracer amount of a naphthylamine of the formula (Ia)

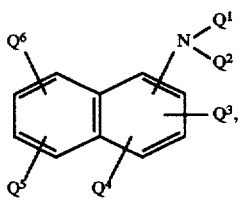

(Ia)

where
- $Q^1$ and $Q^2$ are each, independently of one another, hydrogen, $C_1$–$C_{18}$-alkyl, which can be interrupted by 1 to 3 oxygen atoms in ether functionalities, $C_5$–$C_7$-cycloalkyl, $C_3$–$C_{18}$-alkenyl, unsubstituted or substituted phenyl, or $Q^1$ and $Q^2$ form, together with the nitrogen atom connecting them, a 5- or 6-membered saturated heterocyclic radical which may have oxygen as further hetero atom, and
- $Q^3$, $Q^4$, $Q^5$ and $Q^6$ are each, independently of one another, hydrogen, $C_1$–$C_8$-alkyl, benzyl, cyano, nitro, $C_1$–$C_4$-alkanoyl, $C_1$–$C_4$-alkanoylamino, benzoylamino, hydroxysulfonyl or a radical of the formula $OZ^1$, $COOZ^1$, $NZ^1Z^2$ or $CONZ^1Z^2$, where $Z^1$ and $Z^2$ are each hydrogen, $C_1$–$C_8$-alkyl, which may be substituted by hydroxyl or phenyl, or $C_5$–$C_7$-cycloalkyl or unsubstituted or substituted phenyl, or $Q^3$ together with $Q^2$ is $C_3$-alkylene, which is unsubstituted or substituted by hydroxyl, and, when the radicals $NR^1R^2$ and $NZ^1Z^2$ are in the peri positions, $R^1$ and $Z^1$ can together also be isopropylidene, excluding 1-aminonaphthalene, 2-aminonaphthalene and 1-(p-$C_{12}$–$C_{15}$-alkylphenylamino) naphthalenes.

6. The mineral oil composition as claimed in claim 5, wherein
- $Q^1$ and $Q^2$ are each, independently of one another, hydrogen, $C_1$–$C_{15}$-alkyl which may be interrupted by 1 to 3 oxygen atoms in ether functionalities, cyclohexyl or unsubstituted or substituted phenyl, and
- two of the $Q^3$, $Q^4$, $Q^5$ and $Q^6$ radicals are each hydrogen and the other two are each, independently of one another, hydrogen, $C_1$–$C_4$-alkyl, $C_1$–$C_4$-alkoxy, hydroxyl, nitro, cyano or carboxyl.

7. The mineral oil composition as claimed in claim 5, wherein $Q^1$ is hydrogen, $Q^2$ is $C_1$–$C_{15}$-alkyl which can be interrupted by 1 to 3 oxygen atoms in ether functionalities, or cyclohexyl, and one of the $Q^3$, $Q^4$, $Q^5$ and $Q^6$ radicals is hydroxyl or $C_1$–$C_4$-alkoxy and the others are hydrogen.

* * * * *